(12) United States Patent
Singleton et al.

(10) Patent No.: US 8,754,130 B2
(45) Date of Patent: Jun. 17, 2014

(54) COMPOSITIONS OF DIBROMOMALONAMIDE AND THEIR USE AS BIOCIDES

(75) Inventors: Freddie L. Singleton, Vernon Hills, IL (US); Bei Yin, Buffalo Grove, IL (US); Eileen F. Warwick, Lansdale, PA (US)

(73) Assignee: Dow Global Technologies LLC, Mildand, MI (US)

( * ) Notice: Subject to any disclaimer, the term of this patent is extended or adjusted under 35 U.S.C. 154(b) by 0 days.

(21) Appl. No.: 13/389,466

(22) PCT Filed: Sep. 27, 2010

(86) PCT No.: PCT/US2010/050341
§ 371 (c)(1),
(2), (4) Date: Feb. 8, 2012

(87) PCT Pub. No.: WO2011/038316
PCT Pub. Date: Mar. 31, 2011

(65) Prior Publication Data
US 2012/0184588 A1  Jul. 19, 2012

Related U.S. Application Data

(60) Provisional application No. 61/246,184, filed on Sep. 28, 2009.

(51) Int. Cl.
*A01N 37/18* (2006.01)
*A61K 31/16* (2006.01)
*A01N 25/00* (2006.01)
*A01N 43/80* (2006.01)
*A61K 31/425* (2006.01)

(52) U.S. Cl.
USPC ................... 514/616; 424/405; 514/372

(58) Field of Classification Search
None
See application file for complete search history.

(56) References Cited

U.S. PATENT DOCUMENTS

| | | | |
|---|---|---|---|
| 3,870,795 A | 3/1975 | Miller et al. | |
| 3,929,562 A * | 12/1975 | Shema et al. | ............ 162/161 |
| 4,163,795 A | 8/1979 | Burk | |
| 4,241,080 A | 12/1980 | Burk | |
| 4,800,082 A | 1/1989 | Karbowski et al. | |
| 5,312,827 A | 5/1994 | Bayer et al. | |
| 2004/0261196 A1 | 12/2004 | Ghosh et al. | |

FOREIGN PATENT DOCUMENTS

| | | |
|---|---|---|
| EP | 0398795 A2 | 11/1990 |
| EP | 0431752 A2 | 6/1991 |
| EP | 1500331 A1 | 1/2005 |
| EP | 2008520 A2 | 12/2008 |
| JP | 2007169222 | 7/2007 |
| WO | 2008/091453 A1 | 7/2008 |
| WO | WO 2008091453 A1 * | 7/2008 ............ C02F 1/44 |

* cited by examiner

*Primary Examiner* — Gina C Justice
*Assistant Examiner* — Michael B Pallay
(74) *Attorney, Agent, or Firm* — Tifani M. Edwards

(57) ABSTRACT

A biocidal composition comprising 2,2-dibromomalonamide and an isothiazolinone-based biocide, and its use for the control of microorganisms in aqueous and water-containing systems.

4 Claims, No Drawings

COMPOSITIONS OF DIBROMOMALONAMIDE AND THEIR USE AS BIOCIDES

CROSS REFERENCE TO RELATED APPLICATIONS

This application is a 35 USC §371 national phase filing of PCT/US2010/050341 filed Sep. 27, 2010, which claims the benefit of U.S. Application No. 61/246,184, filed Sep. 28, 2009.

FIELD OF THE INVENTION

The invention relates to biocidal compositions and methods of their use for the control of microorganisms in aqueous and water-containing systems. The compositions comprise 2,2-dibromomalonamide and an isothiazolinone based biocide.

BACKGROUND OF THE INVENTION

Water systems provide fertile breeding grounds for algae, bacteria, viruses, and fungi some of which can be pathogenic. Microbial contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that yield one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and an isothiazolinone-based biocide of the formula I:

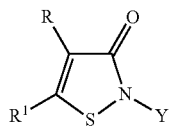

wherein R, $R^1$, and Y are as defined below.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and an isothiazolinone-based biocide of the formula I as shown below. It has surprisingly been discovered that combinations of 2,2-dibromomalonamide and an isothiazolinone-based biocide as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation.

The term "2,2-dibromomalonamide" refers to a compound represented by the following chemical formula:

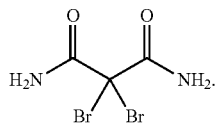

The isothiazolinone-based biocide of the composition of the invention is of the formula I:

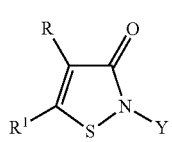

wherein R and $R^1$ are independently hydrogen, halogen or $C_1$-$C_4$ alkyl, or R and $R^1$ together with the carbons to which they are attached from a $C_4$-$C_7$ cycloalkyl ring or an aryl group; and Y is H, $C_1$-$C_{12}$ alkyl, $C_3$-$C_7$ cycloalkyl, aryl or aralkyl.

In some embodiments of the invention, R in formula I is H, or Cl. In some embodiments, $R^1$ is H or Cl. In some embodiments, R and $R^1$, together with the carbons to which they are attached, form phenyl or cyclopentyl.

In some embodiments of the invention, Y in formula I is H, $CH_3$, $CH_2CH_3$, or n-octyl.

In some embodiments, the isothiazolinone based biocide is: 5-chloro-2-methyl-4-isothiazolin-3-one, 2-methyl-4-isothiazolin-3-one, 2-n-octyl-4-isothiazolin-3-one, 1,2-benzisothiazolin-3-one, 4,5-dichloro-2-n-octylisothiazolin-3-one, a mixture of 5-chloro-2-methyl-4-isothiazolin-3-one and 2-methyl-4-isothiazolin-3-one, 2-ethyl-4-isothiazolin-3-one, 5-chloro-2-ethyl-4-isothiazolin-3-one, 4,5-dichloro-2-methyl-4-isothiazolin-3-one, 2-methyl-4,5-trimethylene-4-isothiazolin-3-one, N-methyl-1,2-benzisothiazolin-3-one, or N-butyl-1,2-benzisothiazolin-3-one.

In some embodiments, the isothiazolinone based biocide is: 5-chloro-2-methyl-4-isothiazolin-3-one ("CMIT"), 2-methyl-4-isothiazolin-3-one ("MIT"), 2-n-octyl-4-isothiazolin-3-one ("OIT"), 1,2-benzisothiazolin-3-one ("BIT"), 4,5-dichloro-2-n-octylisothiazolin-3-one ("DCOIT"), or a mixture of 5-chloro-2-methyl-4-isothiazolin-3-one and 2-methyl-4-isothiazolin-3-one, N-methyl-1,2-benzisothiazolin-3-one ("MBIT"), or N-butyl-1,2-benzisothiazolin-3-one ("BBIT").

More than one isothiazolinone compound can be combined for use in the present invention; in such cases, ratios and concentrations are calculated using the total weight of all isothiazolinone compounds present.

Isothiazolinones for use in the invention are commercially available and/or can be readily prepared by those skilled in the art using well known techniques (see e.g., U.S. Pat. No. 5,312,827). 2,2-Dibromomalonamide is commercially available. In some embodiments, it is desirable to formulate the isothiazolinone containing compositions of the invention in solutions containing water or organic solvent or mixtures thereof together with nitrate or nitrite stabilizers to prevent decomposition of the isothiazolinone (see U.S. Pat. No. 3,870,795). In some embodiments, the stabilizer is magnesium nitrate.

In some embodiments of the invention, the weight ratio of 2,2-dibromomalonamide to isothiazolinone-based biocide is between about 100:1 and about 1:400.

In some embodiments, the weight ratio of 2,2-dibromomalonamide to isothiazolinone-based biocide is between about 70:1 and about 1:350.

In some embodiments, the weight ratio of 2,2-dibromomalonamide to isothiazolinone-based biocide is between about 32:1 and about 1:320.

In some embodiments, the isothiazolinone-based biocide is 5-chloro-2-methyl-4-isothiazolin-3-one and the weight ratio of 2,2-dibromomalonamide to the 5-chloro-2-methyl-4-isothiazolin-3-one is from about 100:1 to about 1:20, alternatively from about 70:1 to about 1:10, alternatively from about 40:1 to about 1:5, or alternatively from about 32:1 to about 1:2.

In some embodiments, the isothiazolinone-based biocide is 2-methyl-4-isothiazolin-3-one and the weight ratio of 2,2-dibromomalonamide to the 2-methyl-4-isothiazolin-3-one is from about 20:1 to about 1:20, alternatively from about 10:1 to about 1:10, or alternatively from about 4:1 to about 1:4.

In some embodiments, the isothiazolinone-based biocide is 4,5-dichloro-2-n-octylisothiazolin-3-one and the weight ratio of 2,2-dibromomalonamide to the 4,5-dichloro-2-n-octylisothiazolin-3-one is from about 20:1 to about 1:20, alternatively from about 10:1 to about 1:20, or alternatively from about 4:1 to about 1:16.

In some embodiments, the isothiazolinone-based biocide is 1,2-benzisothiazolin-3-one and the weight ratio of 2,2-dibromomalonamide to the 1,2-benzisothiazolin-3-one is from about 20:1 to about 1:20, alternatively from about 10:1 to about 1:10, alternatively from about 1:1 to about 1:5, or alternatively from about 1:1.6 to about 1:5.

In some embodiments, the isothiazolinone-based biocide is 2-n-octyl-4-isothiazolin-3-one and the weight ratio of 2,2-dibromomalonamide to the 2-n-octyl-4-isothiazolin-3-one is from about 20:1 to about 1:350, alternatively from about 1:1 to about 1:320, alternatively from about 1:2 to about 1:320, or alternatively from about 1:2.5 to about 1:320.

In some embodiments, the isothiazolinone-based biocide is N-methyl-1,2-benzisothiazolin-3-one and the weight ratio of 2,2-dibromomalonamide to the N-methyl-1,2-benzisothiazolin-3-one is from about 20:1 to about 1:280, alternatively from about 1:1 to about 1:256.

In some embodiments, the isothiazolinone-based biocide is N-butyl-1,2-benzisothiazolin-3-one and the weight ratio of 2,2-dibromomalonamide to the N-butyl-1,2-benzisothiazolin-3-one is from about 20:1 to about 1:20, alternatively from about 10:1 to about 1:10, alternatively from about 1:1 to about 1:8, or alternatively from about 1:2 to about 1:8.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water, and air washers), oilfield functional fluids such as drilling muds and fracturing fluids, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and isothiazolinone-based biocide) is typically at least about 1 ppm, alternatively at least about 3 ppm, alternatively at least about 7 ppm, alternatively at least about 10 ppm, or alternatively at least about 100 ppm based on the total weight of the aqueous or water containing system. In some embodiments, a suitable upper limit for the actives concentration is about 1000 ppm, alternatively about 500 ppm, alternatively about 100 ppm, alternatively about 50 ppm, alternatively about 30 ppm, alternatively about 15 ppm, alternatively about 10 ppm, or alternatively about 7 ppm, based on the total weight of the aqueous or water containing system.

The components of the composition can be added to the aqueous or water containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

Growth Inhibition Assay.

The growth inhibition assay used in the examples measures inhibition of growth (or lack thereof) of a microbial consortium. Inhibition of growth can be the result of killing of the cells (so no growth occurs), killing of a significant portion of the populations of cells so that regrowth requires a prolonged time, or inhibition of growth without killing (stasis). Regardless of the mechanism of action, the impact of a biocide (or combination of biocides) can be measured over time on the basis of an increase in the size of the community.

The assay measures the efficacy of one or more biocides at preventing growth of a consortium of bacteria in a dilute mineral salts medium. The medium contains (in mg/l) the following components: $FeCl_3 \cdot 6H_2O$ (1); $CaCl_2 \cdot 2H_2O$ (10); $MgSO_4 \cdot 7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 ul quantities to sterile microtiter plate wells. Dilutions of 2,2-dibromomalonamide ("DBMAL") and/or "Biocide B" are then added to the microtiter plate. After preparing the combinations of actives as illustrated below, each well is inoculated with 100 μl of a cell suspension containing ca. $1 \times 10^6$ cells per milliliter of a mixture of *Pseudomonas aeruginosa*, *Klebsiella pneumoniae*, *Staphylococcus aureus*, and *Bacillus subtilis*. The final total volume of medium in each well is 300 μl. Once prepared as described herein, the concentration of each active ranges from 25 ppm to 0.19 ppm as illustrated in Table 1. The resulting matrix allows testing of eight concentrations of each active and 64 combinations of actives in the ratios (of actives).

before $OD_{580}$ values are collected. The $OD_{580}$ values at $T_0$ are subtracted from $T_{24}$ values to determine the total amount of growth (or lack thereof) that occurs. These values are used to calculate the percent inhibition of growth caused by the presence of each biocide and each of the 64 combinations. A 90% inhibition of growth is used as a threshold for calculating synergy index (SI) values with the following equation:

$$\text{Synergy Index} = M_{DBMAL}/C_{DBMAL} + M_B/C_B$$

where $C_{DBMAL}$: Concentration of DBMAL required to inhibit ~90% of bacterial growth when used alone $C_B$: Concentration of biocide (B) required to inhibit ~90% of bacterial growth when used alone.

$M_{DBMAL}$: Concentration of DBMAL required to inhibit ~90% of bacterial growth when used in combination with biocide (B).

$M_B$: Concentration of biocide (B) required to inhibit ~90% of bacterial growth when used in combination with DBMAL The SI values are interpreted as follows:

SI<1: Synergistic combination

SI=1: Additive combination

SI>1: Antagonistic combination

In the Examples below, the amounts of biocides in the solution are measured in mg per liter of solution (mg/l). Since solution densities are approximately 1.00, the mg/l measurement corresponds to weight ppm. Both units may therefore be used interchangeably in the Examples.

Example 1

DBMAL and CMIT

Table 2 shows the assay results for DBMAL, 5-chloro-2-methyl-4-isothiazolin-3-one ("CMIT"), and combinations. In the assay, the minimum concentration of DBMAL in which

TABLE 1

Template for microtiter plate-based synergy assay showing concentrations of each active. Ratios are based on weight (ppm) of each active.

| | | DBMAL (ppm) | | | | | | | |
|---|---|---|---|---|---|---|---|---|---|
| | | 25.000 | 12.500 | 6.250 | 3.13 | 1.563 | 0.781 | 0.391 | 0.19 |
| Biocide B (ppm) | 25.000 | 1:1 | 1:2 | 1:4 | 1:8 | 1:16 | 1:32 | 1:64 | 1:128 |
| | 12.500 | 2:1 | 1 | 1:2 | 1:4 | 1:8 | 1:16 | 1:32 | 1:64 |
| | 6.250 | 4:1 | 2:1 | 1 | 1:2 | 1:4 | 1:8 | 1:16 | 1:32 |
| | 3.13 | 8:1 | 4:1 | 2:1 | 1 | 1:2 | 1:4 | 1:8 | 1:16 |
| | 1.563 | 16:1 | 8:1 | 4:1 | 2:1 | 1 | 1:2 | 1:4 | 1:8 |
| | 0.781 | 32:1 | 16:1 | 8:1 | 4:1 | 2:1 | 1 | 1:2 | 1:4 |
| | 0.391 | 64:1 | 32:1 | 16:1 | 8:1 | 4:1 | 2:1 | 1 | 1:2 |
| | 0.19 | 128:1 | 64:1 | 32:1 | 16:1 | 8:1 | 4:1 | 2:1 | 1:1 |

Controls (not shown) contain the medium with no biocide added.

Immediately after the microtiter plates are prepared, the optical density (OD) readings for each well is measured at 580 nm and the plates are then incubated at 37° C. for 24 hr. After the incubation period, the plates are gently agitated growth of the consortium is at least 90% less than controls (e.g., $I_{90}$ value) is 12.5 mg/l. The $I_{90}$ value for CMIT is 0.78 mg/l. However, several combinations of the actives are inhibitory below their respective $I_{90}$ values. For example, a combination of 0.19 mg/l DBMAL and 0.38 mg/l CMIT results in 97% inhibition of growth of the microbial consortium.

TABLE 2

Percent inhibition of growth in a species-defined microbial consortium by DBMAL and CMIT alone and combinations of these actives after a 24-hour incubation period. Numbers represent percent inhibition of growth as measured by optical density measurements (OD) at time = 24 hours compared with time = 0 values.

| % Inhibition of growth in Untreated Control | Single Actives (mg/l) | | | | | Combinations of DBMAL and CMIT | | | | | | | |
|---|---|---|---|---|---|---|---|---|---|---|---|---|---|
| | DBMAL Concn. (mg/l) | % Inhibition of growth by DBMAL | CMIT Concn. (mg/l) | % Inhibition of growth by CMIT | DBMAL Concn. (mg/l) | CMIT Concn. (mg/l) | | | | | | | |
| | | | | | | 25.0 | 12.5 | 6.25 | 3.13 | 1.56 | 0.78 | 0.39 | 0.19 |
| 0 | 25.0 | 100 | 25.0 | 98 | 25.0 | 98 | 98 | 96 | 97 | 99 | 100 | 99 | 100 |
| 0 | 12.5 | 98 | 12.5 | 96 | 12.5 | 95 | 98 | 98 | 98 | 99 | 99 | 100 | 100 |
| 3 | 6.25 | 0 | 6.25 | 97 | 6.25 | 96 | 97 | 95 | 98 | 100 | 100 | 99 | 93 |
| 4 | 3.13 | 23 | 3.13 | 98 | 3.13 | 98 | 98 | 97 | 100 | 100 | 100 | 100 | 99 |
| 0 | 1.56 | 15 | 1.56 | 96 | 1.56 | 97 | 99 | 98 | 98 | 98 | 99 | 99 | 92 |
| 2 | 0.78 | 13 | 0.78 | 97 | 0.78 | 98 | 98 | 97 | 98 | 100 | 99 | 92 | 35 |
| 0 | 0.39 | 11 | 0.39 | 10 | 0.39 | 98 | 99 | 100 | 99 | 100 | 80 | 91 | 0 |
| 0 | 0.19 | 5 | 0.19 | 19 | 0.19 | 96 | 97 | 97 | 97 | 99 | 99 | 97 | 2 |

Table 3 shows concentrations of DBMAL and CMIT found to be synergistic. The ratios are based on concentrations of the actives.

TABLE 3

| DBMAL Concn. (mg/l) | CMIT Concn. (mg/l) | Ratio (DBMAL to CMIT) | Synergy Index (SI) |
|---|---|---|---|
| 3.13 | 0.39 | 8:1 | 0.75 |
| 1.56 | 0.39 | 4:1 | 0.62 |
| 0.78 | 0.39 | 2:1 | 0.56 |
| 0.39 | 0.39 | 1:1 | 0.53 |
| 0.19 | 0.39 | 1:2 | 0.51 |
| 6.25 | 0.19 | 32:1 | 0.75 |

TABLE 3-continued

| DBMAL Concn. (mg/l) | CMIT Concn. (mg/l) | Ratio (DBMAL to CMIT) | Synergy Index (SI) |
|---|---|---|---|
| 3.13 | 0.19 | 16:1 | 0.5 |
| 1.56 | 0.19 | 8:1 | 0.37 |

Example 2

DBMAL and MIT

Table 4 shows the assay results for DBMAL, 2-methyl-4-isothiazolin-3-one ("MIT"), and combinations thereof. The $I_{90}$ values for MIT and DBMAL were 25 mg/l and 12.5 mg/l, respectively. Several combinations of the actives are inhibitory below their respective $I_{90}$ values.

TABLE 4

Percent inhibition of growth in a species-defined microbial consortium by MIT and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | | Combinations of DBMAL and MIT | | | | | | | |
|---|---|---|---|---|---|---|---|---|---|---|---|---|---|
| | DBMAL Concn. (mg/l) | % Inhibition of growth by DBMAL | MIT Concn. (mg/l) | % Inhibition of growth by MIT | DBMAL Concn. (mg/l) | MIT Concn. (mg/l) | | | | | | | |
| | | | | | | 25.0 | 12.5 | 6.25 | 3.13 | 1.56 | 0.78 | 0.39 | 0.19 |
| 13 | 25.0 | 100 | 25.0 | 96 | 25.0 | 98 | 98 | 98 | 99 | 98 | 99 | 98 | 96 |
| 0 | 12.5 | 100 | 12.5 | 38 | 12.5 | 98 | 98 | 98 | 98 | 98 | 100 | 99 | 100 |
| 0 | 6.25 | 23 | 6.25 | 16 | 6.25 | 98 | 99 | 97 | 97 | 97 | 0 | 0 | 0 |
| 1 | 3.13 | 0 | 3.13 | 6 | 3.13 | 98 | 99 | 98 | 21 | 0 | 0 | 0 | 0 |
| 2 | 1.56 | 1 | 1.56 | 6 | 1.56 | 96 | 39 | 13 | 1 | 0 | 0 | 0 | 0 |
| 0 | 0.78 | 2 | 0.78 | 0 | 0.78 | 91 | 36 | 6 | 1 | 0 | 0 | 0 | 0 |
| 0 | 0.39 | 6 | 0.39 | 0 | 0.39 | 96 | 37 | 7 | 0 | 0 | 0 | 0 | 1 |
| 0 | 0.19 | 0 | 0.19 | 0 | 0.19 | 98 | 23 | 24 | 0 | 0 | 9 | 7 | 0 |

Table 5 shows concentrations of DBMAL and MIT found to be synergistic. The ratios are based on concentrations of the actives.

TABLE 5

| DBMAL Concn. (mg/l) | MIT Concn. (mg/l) | Ratio (DBMAL to MIT) | Synergy Index (SI) |
|---|---|---|---|
| 6.25 | 6.25 | 0.75 | 1:2 |
| 6.25 | 3.13 | 0.625 | 2:1 |
| 6.25 | 1.56 | 0.56 | 4:1 |
| 3.13 | 12.5 | 0.75 | 1:4 |
| 3.13 | 6.25 | 0.5 | 1:2 |

Table 7 shows concentrations of DBMAL and DCOIT found to be synergistic. The ratios are based on concentrations of the actives.

TABLE 7

| DBMAL Concn (mg/l) | DCOIT Concn. (mg/l) | Ratio (DBMAL to DCOIT) | Synergy Index (SI) |
|---|---|---|---|
| 3.13 | 3.13 | 1:1 | 0.75 |
| 1.56 | 3.13 | 1:2 | 0.63 |
| 0.78 | 3.13 | 1:4 | 0.56 |
| 0.39 | 3.13 | 1:8 | 0.53 |
| 0.19 | 3.13 | 1:16 | 0.52 |
| 6.25 | 1.56 | 4:1 | 0.75 |
| 3.13 | 1.56 | 2:1 | 0.5 |

Example 3

DBMAL and DCOIT

Table 6 shows the assay results for DBMAL, 4,5-dichloro-2-n-octylisothiazolin-3-one ("DCOIT"), and combinations. The $I_{90}$ values for DCOIT and DBMAL were 6.25 mg/l and 12.5 mg/l, respectively. Several combinations of the actives are inhibitory below their respective $I_{90}$ values.

Example 4

DBMAL and BIT

Table 8 shows the assay results for DBMAL, 1,2-benzisothiazolin-3-one ("BIT"), and combinations. The $I_{90}$ value for BIT is 15.63 mg/l and the $I_{90}$ value for DBMAL is 12.5 mg/l. Several combinations of the actives are inhibitory below their respective $I_{90}$ values.

TABLE 6

Percent inhibition of growth in a species-defined microbial consortium by DCOIT and DBMAL alone and combinations of these actives after a 24-hour incubation period. Numbers represent percent inhibition of growth as measured by optical density measurements (580 nm) at time = 24 hours compared with time = 0 values.

| | Single Actives (mg/l) | | | | Combinations of DBMAL and DCOIT | | | | | | | |
|---|---|---|---|---|---|---|---|---|---|---|---|---|
| % Inhibition of growth in Untreated Control | DBMAL Concn. (mg/l) | % Inhibition of growth by DBMAL | DCOIT Concn. (mg/l) | % Inhibition of growth by DCOIT | DBMAL Concn. (mg/l) | DCOIT Concn. (mg/l) | | | | | | |
| | | | | | | 25.0 | 12.5 | 6.25 | 3.13 | 1.563 | 0.781 | 0.391 | 0.19 |
| 12 | 25.0 | 100 | 25.0 | 97 | 25.0 | 100 | 100 | 98 | 98 | 99 | 99 | 99 | 99 |
| 11 | 12.5 | 100 | 12.5 | 99 | 12.5 | 99 | 99 | 98 | 99 | 99 | 100 | 100 | 99 |
| 11 | 6.25 | 28 | 6.25 | 99 | 6.25 | 100 | 99 | 98 | 99 | 99 | 26 | 0 | 0 |
| 12 | 3.13 | 11 | 3.13 | 37 | 3.13 | 100 | 99 | 98 | 98 | 96 | 0 | 0 | 0 |
| 0 | 1.56 | 0 | 1.56 | 41 | 1.56 | 99 | 99 | 100 | 99 | 27 | 0 | 0 | 0 |
| 0 | 0.78 | 6 | 0.78 | 26 | 0.78 | 100 | 100 | 99 | 99 | 0 | 4 | 7 | 12 |
| 0 | 0.39 | 0 | 0.39 | 0 | 0.39 | 100 | 100 | 100 | 100 | 7 | 30 | 20 | 7 |
| 0 | 0.19 | 0 | 0.19 | 0 | 0.19 | 100 | 100 | 100 | 96 | 5 | 30 | 0 | 0 |

TABLE 8

Percent inhibition of growth in a species-defined microbial consortium by BIT and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | % Inhibition of growth by BIT | DBMAL Concn. (mg/l) | Combinations of DBMAL and BIT | | | | | | | |
|---|---|---|---|---|---|---|---|---|---|---|---|---|---|---|
| | DBMAL Concn. (mg/l) | % Inhibition of growth by DBMAL | BIT Concn. (mg/l) | | | | BIT Concn. (mg/l) | | | | | | | |
| | | | | | | | 250.0 | 125.0 | 62.5 | 31.25 | 15.63 | 7.81 | 3.91 | 1.95 |
| 1 | 25.0 | 99 | 250.0 | | 97 | 25.0 | 99 | 99 | 97 | 98 | 99 | 99 | 99 | 99 |
| 0 | 12.5 | 100 | 125.0 | | 98 | 12.5 | 99 | 99 | 98 | 100 | 99 | 100 | 99 | 99 |
| 4 | 6.25 | 45 | 62.5 | | 98 | 6.25 | 98 | 100 | 100 | 100 | 99 | 98 | 98 | 97 |
| 1 | 3.13 | 8 | 31.25 | | 99 | 3.13 | 98 | 100 | 100 | 100 | 100 | 100 | 60 | 0 |
| 0 | 1.56 | 0 | 15.63 | | 96 | 1.56 | 99 | 98 | 100 | 100 | 100 | 97 | 52 | 0 |
| 6 | 0.78 | 1 | 7.81 | | 46 | 0.78 | 99 | 100 | 100 | 100 | 96 | 37 | 10 | 0 |
| 7 | 0.39 | 3 | 3.91 | | 17 | 0.39 | 98 | 98 | 99 | 98 | 64 | 30 | 0 | 0 |
| 0 | 0.19 | 0 | 1.95 | | 0 | 0.19 | 98 | 99 | 96 | 98 | 61 | 30 | 0 | 0 |

Table 9 shows concentrations of DBMAL and BIT found to be synergistic. The ratios are based on concentrations of the actives.

TABLE 9

| DBMAL Concn. (mg/l) | BIT Concn. (mg/l) | Ratio (DBMAL to BIT) | Synergy Index (SI) |
|---|---|---|---|
| 3.13 | 7.81 | 1:2.5 | 0.75 |
| 1.56 | 7.81 | 1:5 | 0.62 |
| 6.25 | 3.91 | 1:1.6 | 0.75 |
| 6.25 | 1.95 | 1:3.2 | 0.62 |

Example 5

DBMAL and OIT

Table 10 shows the assay results for DBMAL, 2-n-octyl-4-isothiazolin-3-one ("OIT"), and combinations. The $I_{90}$ values for OIT and DBMAL were 125 mg/l and 12.5 mg/l, respectively. Several combinations of the actives are inhibitory below their respective $I_{90}$ values.

TABLE 10

Percent inhibition of growth in a species-defined microbial consortium by OIT and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | % Inhibition of growth by OIT | DBMAL Concn. (mg/l) | Combinations of DBMAL and OIT | | | | | | | |
|---|---|---|---|---|---|---|---|---|---|---|---|---|---|---|
| | DBMAL Concn. (mg/l) | % Inhibition of growth by DBMAL | OIT Concn. (mg/l) | | | | OIT Concn. (mg/l) | | | | | | | |
| | | | | | | | 500.0 | 250.0 | 125.0 | 62.5 | 31.25 | 15.63 | 7.81 | 3.91 |
| 8 | 25.0 | 100 | 500.0 | | 100 | 25.0 | 100 | 100 | 100 | 100 | 100 | 100 | 100 | 100 |
| 6 | 12.5 | 100 | 250.0 | | 100 | 12.5 | 100 | 100 | 100 | 100 | 100 | 100 | 100 | 100 |
| 10 | 6.25 | 44 | 125.0 | | 100 | 6.25 | 100 | 100 | 100 | 100 | 100 | 100 | 60 | 0 |
| 0 | 3.13 | 0 | 62.5 | | 64 | 3.13 | 100 | 100 | 100 | 100 | 100 | 1 | 0 | 0 |
| 0 | 1.56 | 1 | 31.25 | | 43 | 1.56 | 100 | 100 | 100 | 100 | 90 | 0 | 0 | 0 |
| 0 | 0.78 | 0 | 15.63 | | 24 | 0.78 | 100 | 100 | 100 | 100 | 40 | 0 | 0 | 0 |
| 0 | 0.39 | 3 | 7.81 | | 7 | 0.39 | 100 | 100 | 100 | 100 | 30 | 1 | 0 | 0 |
| 0 | 0.19 | 0 | 3.91 | | 0 | 0.19 | 100 | 100 | 100 | 100 | 0 | 0 | 0 | 0 |

Table 11 shows concentrations of DBMAL and OIT found to be synergistic. The ratios are based on concentrations of the actives.

TABLE 11

| DBMAL Concn. (mg/l) | OIT Concn. (mg/l) | Ratio (DBMAL to OIT) | Synergy Index (SI) |
|---|---|---|---|
| 3.13 | 62.5 | 1:20 | 0.75 |
| 1.56 | 62.5 | 1:40 | 0.63 |
| 0.78 | 62.5 | 1:80 | 0.56 |
| 0.39 | 62.5 | 1:160 | 0.53 |
| 0.20 | 62.5 | 1:320 | 0.52 |
| 6.25 | 31.25 | 1:5 | 0.75 |
| 3.13 | 31.25 | 1:10 | 0.50 |
| 1.56 | 31.25 | 1:20 | 0.38 |
| 6.25 | 15.63 | 1:2.5 | 0.63 |

Example 6

DBMAL and MBIT

Table 12 shows the assay results for DBMAL, N-methyl-1,2-benzisothiazolin-3-one ("MBIT"), and combinations. The $I_{90}$ values for MBIT and DBMAL were 100.0 mg/l and 12.5 mg/l, respectively. Several combinations of the actives are inhibitory below their respective $I_{90}$ values.

Table 13 shows concentrations of DBMAL and MBIT found to be synergistic. The ratios are based on concentrations of the actives.

TABLE 13

| DBMAL Concn. (mg/l) | MBIT Concn. (mg/l) | Ratio (DBMAL to MBIT) | Synergy Index (SI) |
|---|---|---|---|
| 3.13 | 50 | 1:16 | 0.75 |
| 1.56 | 50 | 1:32 | 0.63 |
| 0.78 | 50 | 1:64 | 0.56 |
| 0.39 | 50 | 1:128 | 0.53 |
| 0.20 | 50 | 1:256 | 0.52 |
| 6.25 | 25 | 1:4 | 0.75 |
| 3.13 | 25 | 1:8 | 0.50 |
| 1.56 | 25 | 1:16 | 0.38 |
| 0.78 | 25 | 1:32 | 0.31 |
| 0.39 | 25 | 1:64 | 0.28 |
| 0.20 | 25 | 1:128 | 0.27 |
| 6.25 | 12.5 | 1:2 | 0.63 |
| 3.13 | 12.5 | 1:4 | 0.38 |
| 1.56 | 12.5 | 1:8 | 0.25 |
| 0.78 | 12.5 | 1:16 | 0.19 |
| 6.25 | 6.25 | 1:1 | 0.56 |

Example 7

DBMAL and BBIT

Table 14 shows the assay results for DBMAL, N-butyl-1,2-benzisothiazolin-3-one ("BBIT"), and combinations. The $I_{90}$ values for BBIT and DBMAL were 50.0 mg/l and 12.5 mg/l, respectively. Several combinations of the actives are inhibitory below their respective $I_{90}$ values.

TABLE 12

Percent inhibition of growth in a species-defined microbial consortium by MBIT and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and MBIT | | | | | | | |
|---|---|---|---|---|---|---|---|---|---|---|---|---|
| | DBMAL Concn. (mg/l) | % Inhibition of growth by DBMAL | MBIT Concn. (mg/l) | % Inhibition of growth by MBIT | DBMAL Concn. (mg/l) | MBIT Concn. (mg/l) | | | | | | |
| | | | | | | 100.0 | 50.0 | 25.0 | 12.5 | 6.25 | 3.13 | 1.56 | 0.78 |
| 2 | 25.0 | 100 | 100.0 | 100 | 25.0 | 100 | 93 | 99 | 95 | 84 | 98 | 85 | 98 |
| 5 | 12.5 | 100 | 50.0 | 67 | 12.5 | 100 | 94 | 91 | 91 | 91 | 100 | 90 | 88 |
| 0 | 6.25 | 44 | 25.0 | 23 | 6.25 | 100 | 97 | 94 | 91 | 98 | 56 | 55 | 0 |
| 15 | 3.13 | 0 | 12.5 | 53 | 3.13 | 100 | 98 | 95 | 92 | 45 | 41 | 10 | 0 |
| 4 | 1.56 | 1 | 6.25 | 26 | 1.56 | 100 | 100 | 93 | 92 | 22 | 0 | 3 | 0 |
| 0 | 0.78 | 0 | 3.13 | 0 | 0.78 | 100 | 100 | 94 | 92 | 35 | 15 | 0 | 0 |
| 4 | 0.39 | 3 | 1.56 | 13 | 0.39 | 100 | 100 | 100 | 81 | 24 | 28 | 0 | 0 |
| 7 | 0.19 | 0 | 0.78 | 16 | 0.19 | 100 | 100 | 91 | 64 | 12 | 28 | 0 | 0 |

TABLE 14

Percent inhibition of growth in a species-defined microbial consortium by BBIT and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and BBIT | | | | | | | |
|---|---|---|---|---|---|---|---|---|---|---|---|---|
| | DBMAL Concn. (mg/l) | % Inhibition of growth by DBMAL | BBIT Concn. (mg/l) | % Inhibition of growth by BBIT | DBMAL Concn. (mg/l) | BBIT Concn. (mg/l) | | | | | | |
| | | | | | | 50.0 | 25.0 | 12.5 | 6.25 | 3.13 | 1.56 | 0.78 | 0.39 |
| 4 | 25.0 | 100 | 50.0 | 100 | 25.0 | 100 | 100 | 93 | 97 | 89 | 99 | 89 | 92 |
| 7 | 12.5 | 93 | 25.0 | 49 | 12.5 | 100 | 100 | 95 | 99 | 91 | 93 | 93 | 93 |
| 9 | 6.25 | 34 | 12.5 | 24 | 6.25 | 100 | 100 | 95 | 62 | 14 | 0 | 0 | 0 |
| 6 | 3.13 | 0 | 6.25 | 32 | 3.13 | 100 | 100 | 50 | 31 | 10 | 0 | 0 | 4 |
| 0 | 1.56 | 0 | 3.13 | 0 | 1.56 | 100 | 76 | 23 | 8 | 0 | 0 | 6 | 0 |
| 0 | 0.78 | 0 | 1.56 | 1 | 0.78 | 100 | 51 | 0 | 0 | 0 | 0 | 0 | 0 |
| 12 | 0.39 | 3 | 0.78 | 0 | 0.39 | 99 | 39 | 3 | 0 | 0 | 0 | 0 | 0 |
| 0 | 0.19 | 0 | 0.39 | 7 | 0.19 | 100 | 74 | 7 | 0 | 0 | 2 | 0 | 0 |

Table 15 shows concentrations of DBMAL and BBIT found to be synergistic. The ratios are based on concentrations of the actives.

TABLE 15

| DBMAL Concn. (mg/l) | BBIT Concn. (mg/l) | Ratio (DBMAL to BBIT) | Synergy Index (SI) |
|---|---|---|---|
| 3.13 | 25 | 1:8 | 0.75 |
| 6.25 | 12.5 | 1:2 | 0.75 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A biocidal composition comprising: 2,2-dibromomalonamide and an isothiazolinone-based biocide of the formula I:

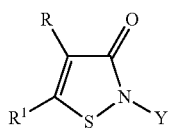

wherein R and $R^1$ are independently hydrogen, halogen or $C_1$-$C_4$ alkyl, or R and $R^1$ together with the carbons to which they are attached from a $C_4$-$C_7$ cycloalkyl ring or an aryl group; and Y is H, $C_1$-$C_{12}$ alkyl, $C_3$-$C_7$ cycloalkyl, aryl or aralkyl wherein the isothiazolinone-based biocide of formula I comprises: 5-chloro-2-methyl-4-isothiazolin-3-one and the weight ratio of 2,2-dibromomalonamide to the 5-chloro-2-methyl-4-isothiazolin-3-one is from 32:1 to 1:2;

2-methyl-4-isothiazolin-3-one and the weight ratio of 2,2-dibromomalonamide to the 2-methyl-4-isothiazolin-3-one is from 4:1 to 1:4;

4,5-dichloro-2-n-octylisothiazolin-3-one and the weight ratio of 2,2-dibromomalonamide to the 4,5-dichloro-2-n-octylisothiazolin-3-one is from 4:1 to 1:16;

1,2-benzisothiazolin-3-one and the weight ratio of 2,2-dibromomalonamide to the 1,2-benzisothiazolin-3-one is from 1:1 to 1:5;

2-n-octyl-4-isothiazolin-3-one and the weight ratio of 2,2-dibromomalonamide to the 2-n-octyl-4-isothiazolin-3-one is from 1:2 to 1:320;

N-methyl-1,2-benzisothiazolin-3-one and the weight ratio of 2,2-dibromomalonamide to the N-methyl-1,2-benzisothiazolin-3-one is from 1:1 to 1:256; or N-butyl-1,2-benzisothiazolin-3-one and the weight ratio of 2,2-dibromomalonamide to the N-butyl-1,2-benzisothiazolin-3-one is from 1:2 to 1:8.

2. A composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration systems, swimming pool water or spa water.

3. A method for controlling microorganism growth in an aqueous or water-containing system, the method comprising treating the aqueous or water-containing system with an effective amount of a composition according to claim 1.

4. A method according to claim 3 wherein the aqueous or water-containing system is paint, coating, aqueous emulsion, latex, adhesive, ink, pigment dispersion, household or industrial cleaner, detergent, dish detergent, mineral slurry polymer emulsion, caulk, tape joint compound, disinfectant, sanitizer, metalworking fluid, construction product, personal care product, textile fluid, spin finish, industrial process water, oilfield functional fluid, fuel, air washer, wastewater, ballast water, filtration system, swimming pool water, or spa water.

* * * * *